United States Patent [19]

Hensens et al.

[11] Patent Number: 4,806,565

[45] Date of Patent: Feb. 21, 1989

[54] ANTIFUGAL TRI-YNE CARBONATES

[75] Inventors: Otto D. Hensens, Red Bank, N.J.; August J. Kempf, Staten Island, N.Y.; Robert E. Schwartz, Westfield, N.J.; Ruth S. Sykes, Edison, N.J.; Carol F. Wichmann, Westfield, N.J.; Kenneth E. Wilson, Westfield, N.J.; Sheldon B. Zimmerman, Springfield, N.J.; Deborah L. Zink, Manalapan, N.J.

[73] Assignee: Merck & Co., Inc., Rahway, N.J.

[21] Appl. No.: 53,920

[22] Filed: May 26, 1987

[51] Int. Cl.$^4$ ................... A61K 31/335; C07D 317/30
[52] U.S. Cl. ...................................... 514/467; 549/229
[58] Field of Search ........................ 549/229; 514/467

[56] References Cited

U.S. PATENT DOCUMENTS

| | | | |
|---|---|---|---|
| 4,331,604 | 5/1982 | Renga et al. | 549/229 |
| 4,332,729 | 6/1982 | Renga et al. | 549/229 |

Primary Examiner—Glennon H. Hollrah
Assistant Examiner—Susan P. Treanor
Attorney, Agent, or Firm—Richard S. Parr; Hesna J. Pfeiffer

[57] ABSTRACT

The invention relates to a novel tri-yne carbonate of formula I. Such compound can be produced by isolating it from the fermentation broth of ATCC-53614, ATCC-53615 OR ATCC-53616. The tri-yne carbonate has antifungal activity.

12 Claims, 1 Drawing Sheet

ANTIFUGAL TRI-YNE CARBONATES

BACKGROUND OF THE INVENTION

The invention relates to a novel tri-yne carbonate of formula I. Such compound can be produced by isolating it from the fermentation broth of ATCC-53614, ATCC-53615 or ATCC-53616. The tri-yne carbonate has antifungal activity.

SUMMARY OF THE INVENTION

This invention relates to the novel compound 5-(1-hydroxy-2,4,6-heptatriynyl)-2-oxo-1,3 dioxolane and its pharmaceutically acceptable salts having the general structure of formula I:

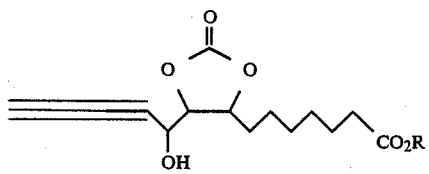

wherein R is H or a pharmaceutically acceptable salt.

DETAILED DESCRIPTION OF THE INVENTION

Figure 1:
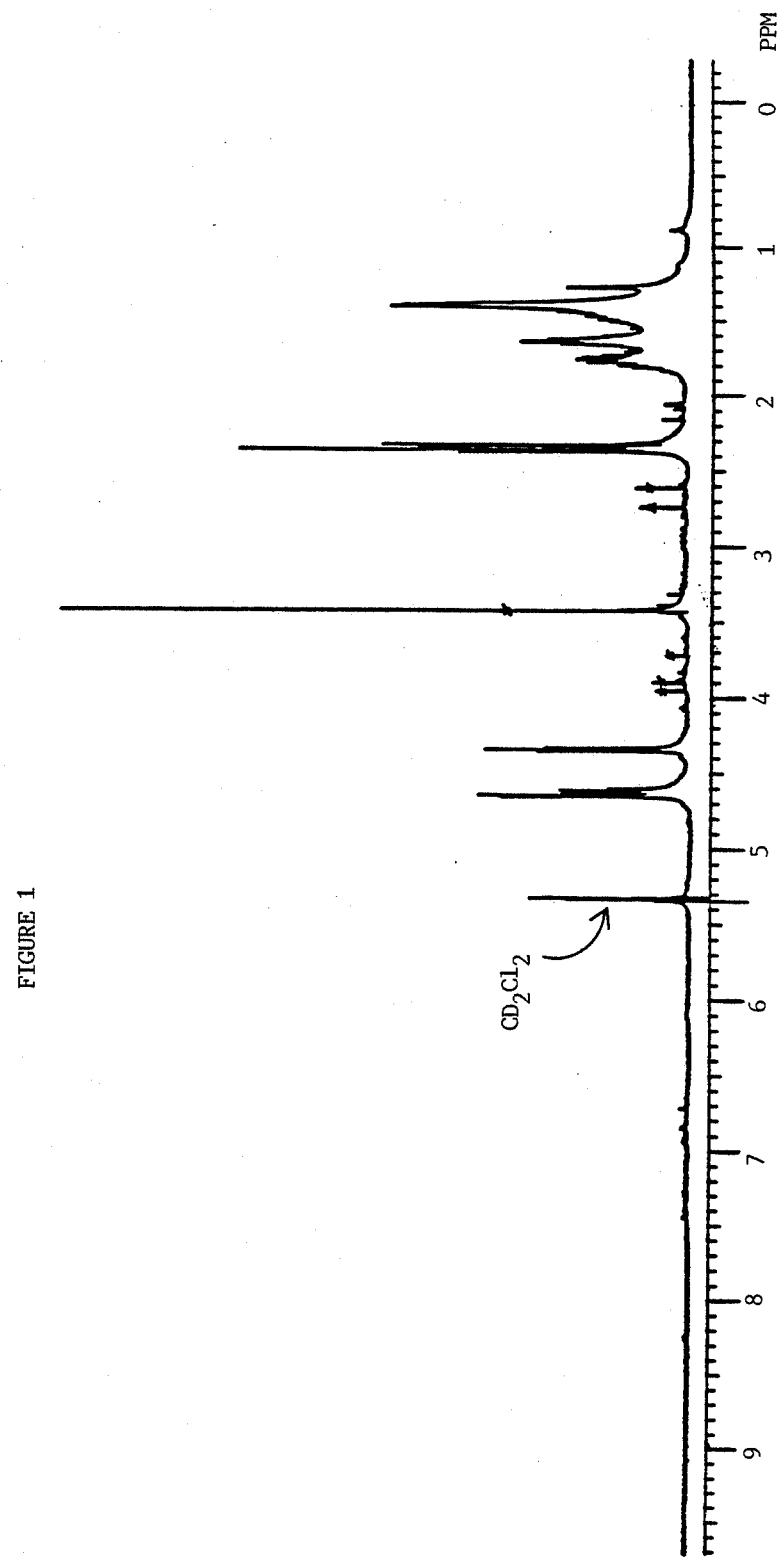

The tri-yne carbonate of Formula I has antifungal activity. Specifically the compounds of this invention are useful as antifungal agents against pathogenic fungi systemic to and upon the exterior of humans and animals; against agricultural fungi affecting living plants; and against surface fungi on inanimate objects.

They may be administered to humans and animals topically, orally or parenterally in the form of a medicated liquid, paste or powder, a capsule, a tablet, an injectable preparation or the like. It is usually desirable to use the oral route. Formulations containing the active ingredients are readily prepared. Doses may be varied, depending on the ae, severity, body weight and other conditions of human patients but daily dosage for adults is within a range of from about 10 mg/kg to 500 mg/kg (preferably 25 to 100 mg/kg) which may be given in two to four divided doses. Higher doses may be favorably employed as required. Topically, the antifungal agents may be administered at a dosage of from 0.25 to 5 percent of a suitable topical preparation.

The compounds are useful against pathogenic mycotic infections upon the surface of or systemic within the body of living animals such as fungi of the Trichophyton spp. species, Crypotococcus spp., Hormodendrum spp., Geotrichum spp., Candida spp., and the like.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

As used in the instant invention "fungicide" is intended to include controlling fungi broadly so as to include the killing of fungi as well as inhibiting the growth of fungi.

Fields of technology adversely affected by the lack of effective fungicides are many and include the paint, wood, textile, cosmetic, leather, tobacco, fur, rope, paper, pulp, plastics, fuel, rubber and food industries. Fungicides are also utilized for agricultural application, for instance in preventing or minimizing fungus growth on plants, fruits, seeds or soil.

Although many antifungal agents have been described and used heretofore in an effort to control fungi, none are entirely satisfactory and continued losses resulting from fungal attack make the problem of control a serious and lasting one. The number of fungicides practically useful in combatting fungal growth have been small and only in a few cases have synthetic organic chemicals been found applicable.

The compounds of the invention are effective in controlling the growth of Asperqillus species, for example *A. niger, A. flavus, A. fumiqatus, A. oryzae, A. luchensis, A. versicolor, A. sydowi, A. nidulans, A. flaucus* and *A. terreus,* Penicillium species, for example *P. notatum, P. roqueforti, P. chrysogenum, P. oxalicum, P. spinulosum, P. martensii, P. citrinium, P. diqitatum, P. expansum, P. italicum, P. cyclopium,* and *P. funiculosum,* Neurospora species such as *N. sitophila,* Phoma species such as *P. terrestrius,* Rhizopus species, Alternaria species such as *A. solani,* Chaetomium species such as *C. globosum,* Chaetomicum species, for example, *C. clivaceum,* and Monilia species such as *M. sitophila* and *M. nigra.* The above fungi may be found on cosmetics, leather, electrical insulation, textiles, and numerous other materials capable of supporting their growth.

The compounds of this invention may be employed in treatment of plants, soils, fruits, seeds, fur, wood and the like. The fungicidal compounds can be used against soil fungi, such as *Rhizoctonia solani, Fusarium solani,* and *Pythium ultimum,* plant fungi, for instance *Erysiphe polygoni, Alternaria solani* and *Cochliobolus miyabanus* as well as against saprophytes known to attack wood, pulp and lumber such as *Lenzites trabea* and *Ceratocystis pilifera* and the fungus *Pullularia pullulans* which attacks paint.

In particular the compounds of this invention are useful in controlling those agricultural fungus infections that attack growing plants. The compounds are particularly effective against those fungi that cause rice blast, tomato late blight, tomato early blight, wheat leaf rust, bean powdery mildew and tomato Fusarium wilt.

It should be understood that the compounds may be utilized in diverse formulations, solid, including finely divided powders and granular materials as well as liquid, such as solutions, emulsions, suspensions, concentrates, emulsifiable concentrate, slurries and the like, depending upon the application intended and the formulation media desired.

Thus, it will be appreciated that compounds of this invention may be employed to form fungistatic compositions containing such compounds as essentially active ingredients thereof, which compositions may also include finely divided dry or liquid diluents, extenders, fillers, conditioners and excipients, including various clays, diatomaceous earth, talc, and the like, or water and various organic liquids such as lower alkanols, for example ethanol and isopropanol, or kerosene, benzene, toluene and other petroleum distillate fractions or mixtures thereof.

When the active agents are employed in preventing topical fungal growth, one or more of the compounds may be uniformly distributed in a vehicle that is chemically compatible with the particular compound selected, noninhibiting with respect to the action of the antifungal and essentially noninjurious to body tissue under the conditions of use.

It is also important that the compound of formula I is efficacious against medically important fungi, especially yeast-like fungi, for example, *Cryptococcus neoformans, Candida albicans, Ca. parapsilosis, Ca. tropicalis, Ca. pseudotropicalis, Ca. krusei, Ca. rugosa, Ca. quilliermondii, Ca. stellatoidea, Torulopsis glabrata, Saccharomyces cerevisiae, Aspergillus fumigatus, A. flavus* and *Penicillium italicum*.

The compound of formula I can be prepared by growing under controlled conditions the microorganism ATCC-53614, ATCC-53615 or ATCC-53616, with ATCC-53614 being preferred because it produces the largest quantities of the compound of formula I. The compound is obtained by fermentation of one of said microorganisms followed by isolation of the compound, all as described hereinbelow.

Based upon taxonomic studies, ATCC 53614 and ATCC 53615 are new strains of the species *Streptoverticillium hiroshimense*. ATCC-53616 is a strain of the genus *Nocardia*. A sample of ATCC-53614, ATCC-53615 and ATCC-53616 has been deposited, without restriction as to availability, in the permanent culture collection of the American Type Culture Collection at 12301 Parklawn Drive, Rockville, Md. 20852 and have been assigned the accession numbers that such microorganisms have been referred to herein.

The morphological and cultural characteristics of ATCC-53614, ATCC-53615 and ATCC-53616 are as follows: (V=vegetative growth, A=aerial mycelium, SP=soluble pigment)

ATCC-53615

Morphology: Sporophores form short branches produced in a verticil or whorl at intervals along the aerial mycelium. These branches in turn produce several secondary branches that form straight chains of 10-15 spores. Spores are cylindrical, 0.9×1.2-1.7 microns. Spore surface is smooth.

Yeast extract-malt extract agar (ISP Medium 2)
   V: Reverse—dark brown with vectors of dark red
   A. Deep pink mixed with red and rose-beige vectors
   SP: None
Oatmeal agar (ISP Medium 3)
   V: Reverse—dark brown with vectors of dark red
   A: Velvety, dark pink with pinkish-white & rose-beige vectors and red flecks
   SP: None
Inorganic salts-starch agar (ISP Medium 4)
   V: Reverse—dark reddish brown with vectors of deep pink
   A: Deep pink mixed with rose-beige and white
   SP: None
Glycerol asparagine agar (ISP Medium 5)
   V: Reverse—dark reddish brown
   A: Rose-beige with vectors of deep rose
   SP: None
Peptone-iron-yeast extract agar (ISP Medium 6)
   V: Brown
   A: None
   SP: Medium brown
   Melanin: Dark brown pigment produced in tryptone-yeast extract broth, light brown pigment produced in tyrosine agar and peptone-iron-yeast extract agars Tyrosine Agar (ISP Medium 7)
   V: Reverse—brown edged with reddish-brown
   A: rose-beige mixed with pink and white
   SP: Medium brown
Czapek-Dox Agar
   V: Colorless, flat
   A: Sparse, white
   SP: None Carbon utilization
   Pridham-Gottlieb basal medium (ISP Medium 9) + 1% carbon source;
   + = growth; ± = growth poor or questionable;
   − = no growth as compared to negative control (no carbon source)

| | |
|---|---|
| Glucose | + |
| Arabinose | − |
| Cellulose | − |
| Fructose | ± |
| Inositol | + |
| Lactose | ± |
| Maltose | + |
| Mannitol | − |
| Mannose | + |
| Raffinose | ± |
| Rhamnose | − |
| Sucrose | ± |
| Xylose | ± |

Temperature range (Yeast extract-dextrose + salts agar)

| | |
|---|---|
| 28° C. | Good growth and sporulation |
| 37° C. | good vegetative growth; moderate aerial growth |
| 42° C. | Moderate vegetative growth; no aerial |
| 50° C. | No growth |

Oxygen requirements (Stab culture in yeast extract-dextrose + salts agar)
   Aerobic All readings taken after three weeks at 28° C. unless noted otherwise. pH of all media approximately neutral (6.8–7.2).

Color number designations taken from Color Harmony Manual, 1958, 4th Edition, Container Corporation of America, Chicago, Ill.

ATCC-53614

Morphology: Sporophores form short branches produced in a verticil or whorl at intervals along the aerial mycelium. These branches in turn produce several secondary branches that form straight chains of 10-15 spores. Spores are cylindriacal, 0.9×1.2-1.7 microns (970×). Spore surface is smooth (TEM).

Yeast extract-malt extract agar (ISP Medium 2)
   V: Reverse—dark red
   A. Rose-beige
   SP: None
Oatmeal agar (ISP Medium 3)
   V Reverse—deep red
   A: Rose-beige
   SP: None
Inorganic salts-starch agar (ISP Medium 4)
   V: Reverse—deep red
   A: Rose-beige
   SP: None
Glycerol asparagine agar (ISP Medium 5)
   V: Reverse—dark brown with flecks and vectors of deep red
   A: Pinkish-beige mixed with white and vector of deep pink
   SP: None
Peptone-iron-yeast extract agar (ISP Medium 6)

V: Tan with red flecks
A: None
SP: Lt. brown
Melanin: Positive on peptone-iron-yeast extract agar and tryptone—yeast extract broth
Tyrosine Agar (ISP Medium 7)
 V: Reverse—dark red with vectors of lighter red
 A: Pinkish-white with vectors of light pink
 SP: very light brown
Czapek-Dox Agar
 V: moderate, white
 A: moderate, white
 SP: None Carbon utilization
 Pridham-Gottlieb basal medium (ISP Medium 9) + 1% carbon source;
 + = growth; ± = growth poor or questionable;
 − = no growth as compared to negative control (no carbon source)

| | |
|---|---|
| Glucose | + |
| Arabinose | ± |
| Cellulose | − |
| Fructose | + |
| Inositol | + |
| Lactose | ± |
| Maltose | + |
| Mannitol | + |
| Mannose | + |
| Raffinose | ± |
| Rhamnose | − |
| Sucrose | ± |
| Xylose | ± |

Temperature range (Yeast extract-dextrose + salts agar)

| | |
|---|---|
| 28° C. | Good growth and sporulation |
| 37° C. | Moderate growth and sporulation |
| 42° C. | No growth |
| 50° C. | No growth |

Oxygen requirements (Stab culture in yeast extract-dextrose + salts agar)
 Aerobic All readings taken after three weeks at 28° C. unless noted otherwise. pH of all media approximately neutral (6.8–7.2).

Color number designations taken from Color Harmony Manual, 1958, 4th Edition, Container Corporation of America, Chicago, Ill.

ATCC-53616

Morphology: Vegatative hyphae were fully developed with branching. Fragmentation of hyphae occured in older cultures.

Yeast extract-malt extract agar (ISP Medium 2)
 V: Reverse—dull golden yellow
 A. Moderate, whitish
 SP: None
Oatmeal agar (ISP Medium 3)
 V: Tan
 A: sparse, grayish white
 SP: None
Inorganic salts-starch agar (ISP Medium 4)
 V: Reverse—dull golden-yellow
 A: Moderate, white to creamish-white
 SP: None
Glycerol asparagine agar (ISP Medium 5)
 V: Tan
 A: Sparse, whitish
 SP: None
Peptone-iron-yeast extract agar (ISP Medium 6)
 V: Tan
 A: None
 SP: None
 Melanin: Negative
Tyrosine Agar (ISP Medium 7)
 V: Tan
 A: None
 SP: None
Czapek-Dox Agar
 V: Very thin, colorless growth
 A: None
 SP: None Carbon utilization
 Pridham-Gottlieb basal medium (ISP Medium 9) + 1% carbon source; + = growth; ± = growth poor or questionable; − = no growth as compared to negative control (no carbon source)

| | |
|---|---|
| Glucose | + |
| Arabinose | − |
| Cellulose | − |
| Fructose | + |
| Inositol | + |
| Lactose | − |
| Maltose | + |
| Mannitol | − |
| Mannose | + |
| Raffinose | − |
| Rhamnose | − |
| Sucrose | − |
| Xylose | − |

Temperature range (Yeast extract-dextrose + salts agar)

| | |
|---|---|
| 28° C. | Good vegetative and aerial growth |
| 37° C. | Good vegetative; sparse aerial |
| 42° C. | No growth |
| 50° C. | No growth |

Oxygen requirements (Stab culture in yeast extract-dextrose + salts agar)
 Aerobic All readings taken after three weeks at 28° C. unless noted otherwise. pH of all media approximately neutral (6.8–7.2).

It is to be understood that for the production of the compound of formula I, the present invention is not limited to the use of ATCC-53614, ATCC-53615 or ATCC-53616. It is especially desired and intended to include the use of natural or artificial mutants produced from the described organisms, or other variants of ATCC-53614, ATCC-53615 or ATCC-53616 as far as they can produce the compound of formula I. The artificial production of mutants may be achieved by a conventional operation such as X-ray or ultraviolet (UV) radiation, or by the use of chemical mutagens such as; nitrogen mustards, nitrosoguanidine, camphor and the like, or by means of recombinant DNA technology.

The compound of formula I can be produced by utilizing a preserved source of ATCC-53614, ATCC-53615 or ATCC-53616 under controlled aerobic conditions in a liquid nutrient medium as follows. The preserved source is utilized to inoculate a liquid nutrient medium containing sources of carbon, nitrogen, phosphorus, calcium and magnesium and other elements necessary for life. This medium is incubated at 28° C. The flask containing the culture and liquid nutrient medium is incubated with agitation on a rotary shaker at 220 RPM. After 48 hours, when growth is abundant, the culture growth is used to inoculate a flask containing a medium which supports production of the product.

These production media are inoculated with the culture growth and are incubated at 28° C. for 4 days with agitation at 180 to 220 RPM, most often 220 RPM.

Such media contain carbon sources such as glycerol, dextrose, cottonseed oil, cod liver oil or corn gluten. They contain nitrogen and sulfur sources such as beef extract, yeast extract, ardamine pH, Edamine, Hycase and corn gluten. Also included are inorganic ions such as calcium, as well as some inert materials as celite.

In order to isolate the compound of formula I, the fermentation broth must be clarified by filtration. The compounds of interest reside in the broth filtrate. The crude product may be purified by chromatography using an appropriate adsorbent such as polymeric organic based resins such as Amberlite XAD-2 or Mitsubishi HP-20, silica gel and hydroxypropyl cross linked dextran gels such as Pharmacia LH-20. The compound of formula I is eluted from the adsorbents with suitable solvents or mixture of solvents. Solvent extraction is also used.

The following examples illustrate the preparation of the compound of the invention and should not be construed as limiting the invention.

The composition of media employed in the following examples are listed below. Media are prepared in a 250 ml Erlenmeyer flask. The contents are sterilized with steam at 121° C., 15 pounds pressure for 20 minutes.

| BAM II & Celite | |
|---|---|
| Yeast Extract | 1 g. |
| Beef Extract | 1 g. |
| Hycase | 2 g. |
| Glucose | 10 g. |
| MOPS | 11.6 g. |
| Celite | 5 g. |
| Distilled H$_2$O | 1,000 ml. |
| pH | 7.0–7.2 using NaOH |
| NPA-2 | |
| Corn Gluten | 5 g. |
| Edamine | 2.5 g. |
| Yeast Extract | 5 g. |
| Glucose | 10 g. |
| CaCO$_3$ | 5 g. |
| Distilled H$_2$O | 1,000 ml. |
| pH | 7.2–7.4 using NaOH |
| KH | |
| Tomato Paste | 20 g. |
| Primary Yeast | 10 g. |
| Dextrin | 20 g. |
| CoCl$_2$.6H$_2$O | 5 g. |
| Distilled H$_2$O | 1,000 ml. |
| pH | 7.2–7.4 using NaOH |
| KE | |
| Dextrose | 1 g. |
| Starch | 10 g. |
| Beef Extract | 3 g. |
| Ardamine pH | 5 g. |
| NZ Amine Type E | 5 g. |
| MgSO$_4$.7H$_2$O | 0.05 g. |
| Phosphate Buffer | 2.0 ml. |
| CaCO$_3$ | 0.5 g. |
| Distilled H$_2$O | 1,000 ml. |
| pH | 7.0–7.2 using NaOH |
| Phosphate Buffer | |
| KH$_2$PO$_4$ | 91 g. |
| Na$_4$HPO$_4$ | 95 g. |
| Distilled H$_2$O | 1,000 ml. |
| pH = 7 | |
| LP | |
| Beef Extract | 6 g. |
| Glycerol | 8.0 ml. |
| Cottonseed Oil | 1.0 ml. |
| Cod Liver Oil | 1.0 ml. |
| Ardamine pH | 0.4 g. |
| Distilled H$_2$O | 1,000 ml. |
| pH = 7.0 | |

EXAMPLE 1

Preparation of the Compound of Formula I (I) (a) Fermentation of ATCC-53614

A culture of ATCC-53614 is inoculated from an L-tube (lyophilized tube) into a 250 ml baffled erlenmeyer flask containing 44 ml. KE seed medium and grown for two days at 28° C. and shaken in a rotary shaker (2 inch throw) at 220 rpm. Two ml of the grown seed medium is then inoculated into a 250 ml unbaffled erlenmeyer flask containing about 54 ml. of the production medium LP and grown at 28° C. and shaken in a rotary shaker (2 inch throw) for four days at 220 rpm. The compound of formula I is contained in this broth.

(b) Fermentation of ATCC-53615

A culture of ATCC-53615 is inoculated from an L-tube into a 250 ml erlenmeyer flask containing 54 ml of BAMII and celite seed medium. The flask is incubated at 28° C. and shaken in a rotary shaker (2 inch throw) at 220 rpm for 48 hours. Then 10 ml from this flask is used to inoculate a two liter baffled erlenmeyer flask containing 250 ml of NPA-2 production medium. This flask is incubated at 28° C., and shaken in a rotary shaker (2 inch throw) for 96 hours at 180 rpm. The compound of formula I is contained in this broth.

(c) Fermentation of ATCC-53616

A culture of ATCC-53616 is inoculated from an L-tube into a 250 ml baffled erlenmeyer flask containing 54 ml of KE medium. The flask was then placed on a rotary shaker (2 inch throw) and shaken at 220 rpm for 2 days in a 28° C. room. Two ml of the broth were then used to inoculate a 250 ml unbaffled erlenmeyer flask containing 44 ml of KH medium. This flask was then placed on a rotary shaker (2 inch throw) at 28° C. and shaken for four days at 220 rpm.

(II) Isolation of the Compound of Formula I

The compound of formula I can be isolated from each of the broths of ATCC-53614, ATCC-53615 and ATCC-53616 by the following procedure. It should be noted that the following isolation procedure can be utilized for varying volumes of whole broth by aadjusting proportionately the volumes of the solvents and adsorbents.

EXAMPLE: ISOLATION OF THE FREE ACID OF FORMULA I (a) Approximately 2180 L of whole broth from a fermentation batch was harvested at 48 hours. The broth was clarified by filtration using Supercel as a filter aid, followed by a water wash. The 2200 L filtered broth at pH7 was adsorbed on 120 L of Mitsubishi Diaion HP-20 resin at 4 L/minute. The resin was washed with 120 L of distilled deionized water at the same rate. Antibiotic activity was eluted from the resin with 15×10 L fractions of 60:40 acetone-water. The rich eluate fractions (5–12) were combined (80 L) and extracted with 2×80 L ethyl acetate. Extract 1 (130 L) and extract 2 (100 L) were combined and dried over anhydrous sodium sulfate. The drying agent was removed by filtration and the filtrate was concentrated under vacuum to 3.75 L. The concentrated extract contained 6.5 g of the free acid of formula I at about 5% pure.

(b) 800 ml of ethylacetate extract (approximately 1.39 g of the free acid of formula I) from Step a was evaporated to an oily residue and immdiately taken up in methylene chloride to a volume of 100 ml. The methylene chloride solution was applied to a 200 g column of E. Merck silica gel grade 62 (60–200 mesh), equilibrated in methylene chloride. The column was washed with 2×500 ml of methylene chloride and then eluted with 5:95 methanol-methylene chloride, taking 250 ml fractions. The free acid of formula I was eluted with the 5:95 methanol-methylene chloride. Fractions 3 and 4 contained 1.0 g (~70% yield) of the free acid of formula I at ~10% pure.

(c) The silica gel rich eluates 3 and 4 from Step b were evaporated to about 12 ml (methanol). 120 ml of methylene chloride and 120 ml of hexane was added to provide the feed for a 900 ml Pharmacia Sephadex LH-20 column equilibrated in 10:10:1 hexane-methylene chloride-methanol. After a 360 ml void volume fraction, four 900 ml (1 column volume) fractions and 30×250 ml fractions were collected. Based on HPLC and bioassay, fraction 13–25 (250 ml each) contained 0.9 g of substantially pure free acid of formula I.

(d) Due to the instability of free acid of formula I to concentration, an alternate method was used to provide concentrated solutions. LH20 fractions 13–25 from Step C, 3250 ml, was extracted with 500 ml of 0.1 M potassium phosphate buffer pH 7.2. The compound was extracted into the aqueous layer, 620 ml, which was reextracted with 200 ml of methylene chloride at pH 4.5. The methylene chloride extract was dried over anhydrous sodium sulfate. The extraction volumes could be adjusted to provide varying concentrations of the free acid of the compound of formula I in methylene chloride.

(e) Preparation of Sodium Salt of the Compound of Formula I

In order to provide aqueous solutions of the sodium salt of the compound of formula I, the following method was used. 110 ml of LH-20 rich cut (10:10::1) was extracted with 50 ml of water, the pH carefully adjusted to 7.5 with dilute sodium hydroxide. The aqueous layer was evaporated under reduced pressure to remove residual organic solvent, yielding an aqueous solution of the sodium salt of the compound of formula I.

III Analytical Data

All three isolates were shown by HPLC and HRMS to be identical.

Analytical data for the compound of formula I isolated from ATCC-53616 is as follows:

1. Mass Spectral Data

Mass spectral data were obtained on MAT 212 mass spectrometer at 90 ev in the electron impact mode. High resolution data were obtained on the same instrument using the peak matching method.

HRMS gave a molecular formula $C_{17}H_{18}O_6 \cdot T_2$ (calc. 462.1894; found 462.1882) upon trimethylsilylation with pyridine: BSTFA (1:1) at 100° C. for 1 hour. Abundant mass ions were found at m/z 175.0574 corresponding to $C_7H_3O \cdot T_1$ (calc. 175.0579). [$T = C_3H_8Si = 72.0395$].

2. $^1H$ NMR Spectrum

The spectrum is in FIG. I. The spectrum has been recorded in $CD_2Cl_2$ at ambient room temperature on a Varian XL400 spectrometer. Chemical shifts are shown in ppm relative to tetramethylsilane (TMS) at zero ppm using the solvent peak at $\delta 5.32$ as internal reference.

3. $^{13}C$ NMR Data

The spectrum was recorded in $CD_2Cl_2$ at ambient room temperature at 75 MHz on a Varian XL400 spectrometer. Chemical shifts are given in ppm relative to tetramethylsilane at zero ppm using the solvent peak at 53.8 ppm as internal reference.

In agreement with HRMS data, 17 carbons are observed with the following chemical shifts: 24.4, 24.8, 28.90, 28.95, 33.8, 34.8, 59.0, 63.2, 64.3, 67.7, 69.0, 71.9, 72.9, 78.7, 81.7, 154.1, 178.0 ppm Infrared Data A difference infrared spectrum was measured in dichloromethane on a Nicolet FT-lR instrument, model 7199. Strong bands were observed at 1806 (carbonate) and 1742 (COOH) $cm^{-1}$

EXAMPLE 2

Antifungal Activity

The antifungal activity of the free acid of formula I was determined by an agar dilution assay as follows:

The compound of formula I was added to cooled, molten yeast nitrogen base plus glucose agar (1.0 ml of drug plus 9.0 ml agar). Appropriate solvent and media controls (drug free) also were prepared. Prepared plates were stored in the dark at room temperature overnight prior to use.

The yeast cultures, maintained in yeast maltose (YM) broth, were transferred to fresh YM medium and incubated overnight at 37° C. with shaking (250 rpm). After incubation, each culture was diluted in sterile saline to yield final concentrations of $3 \times 10_5$ to $3 \times 10^6$ colony forming units (CFU)/ml. The isolates of Asoergillus and Penicillium were maintained on potato dextrose agar slants and spore suspensions made following vigourous shaking with sterile glass beads. The spore preparations were used as the inocula for these three filamentous fungi.

Each prepared plate was inoculated with 21 yeast-like and filamentous fungi using a Denley Multipoint Inoculator (Denley, Sussex, England). The inoculator delivers approximately 0.001 ml to the agar surface resulting in inoculation of from $3 \times 10^2$ to $3 \times 10^3$ CFUs. The plates were incubated at 28° C. for 48 hours. The minimum inhibitory concentrations (MICs) were recorded as the lowest concentration of drug showing no growth or less than three CFU/spot.

The results were as follows:

| FUNGUS | | MINIMUM INHIBITORY CONCENTRATION (UG/ML) |
| --- | --- | --- |
| Crypotococcus neoformans | MY1051 | 1.88 |
| Cr. neoformans | MY1146 | 3.75 |
| Candida albicans | MY1058 | 0.47 |
| Ca. albicans | MY1055 | 0.47 |
| Ca. albicans | MY0992 | 7.50 |
| Ca. albicans | MY1013 | 0.47 |
| Ca. albicans | MY1029 | 0.47 |
| Ca. parapsilosis | MY1009 | 1.88 |
| Ca. parapsilosis | MY1010 | 0.47 |
| Ca. tropicalis | MY1011 | 15.0 |
| Ca. tropicalis | MY1012 | 1.88 |
| Ca. pseudotropicalis | MY1040 | 0.94 |
| Ca. krusei | MY1020 | 30.0 |
| Ca. rugosa | MY1022 | 7.5 |
| Ca. quilliermondii | MY1019 | 7.5 |
| Ca. stellatoidea | MY1018 | 7.5 |
| Torulopsis glabrata | MY1059 | 1.88 |
| Saccharomyces cerevisiae | MY1027 | 1.88 |
| Aspergillus fumigatus | MF4839 | >30.0 |
| A. flavus | MF0383 | >30.0 |
| Penicillium italicum | MF2819 | 7.5 |

What is claimed is:

1. A compound having the structural formula:

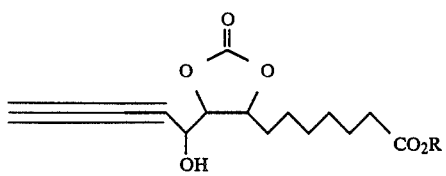

wherein R is hydrogen or a pharmaceutically acceptable salt.

2. A method of inhibiting fungal growth which comprises the administration to or upon a subject or an object in need of such treatment, a non-toxic therapeutically effective amount of a compound represented by the following structural formula:

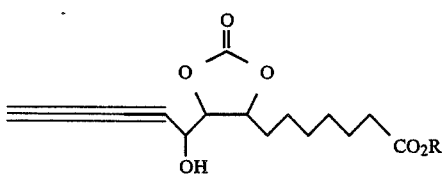

wherein R is hydrogen or a pharmaceutically acceptable salt.

3. The method of claim 2 wherein the fungus to be controlled is within or upon a living animal.

4. The method of claim 2 wherein the fungus to be controlled is upon a plant.

5. The method of claim 2 wherein the fungus to be controlled is upon an inanimate object.

6. The method of claim 3 in which a daily dosage of from about 10 to 500 mg/kg of active ingredient is administered.

7. The method of claim 6 in which the active ingredient is administered with a pharmaceutical carrier.

8. The method of claim 7 in which the administration is oral.

9. A method of claim 7 in which the administration is parenteral.

10. An antifungal composition comprising a non-toxic therapeutically effective amount of a compound represented by the following structural formula:

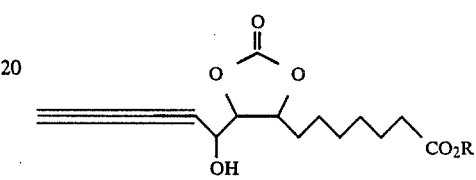

wherein R is hydrogen or a pharmaceutically acceptable salt in an inert carrier.

11. The composition of claim 10 which is a solid.

12. The composition of claim 10 which is a liquid.

* * * * *

Notice of Adverse Decision in Interference

In Interference No. 102,279, involving Patent No. 4,806,565, O. D. Hensens, A. J. Kempf, R. E. Schwartz, R. S. Sykes, C. F. Wichmann, K. E. Wilson, S. B. Zimmerman, D. L. Zink, ANTIFUGAL TRIYNE CARBONATES, final judgment adverse to the patentees was rendered Mar. 28, 1990, as to claims 1-12.

(*Official Gazette May 8, 1990*)